(12) United States Patent
Yonce (10) Patent No.: US 12,048,913 B2
(45) Date of Patent: Jul. 30, 2024

(54) PRODUCTS FOR TREATING INFLAMMATION, INFECTIONS, DISEASE, AND MALODORS CONTAINING ADSORBENT POROUS CARBONACEOUS MATERIAL

(71) Applicant: Angela Jean Yonce, Petal, MS (US)

(72) Inventor: Angela Jean Yonce, Petal, MS (US)

( * ) Notice: Subject to any disclaimer, the term of this patent is extended or adjusted under 35 U.S.C. 154(b) by 438 days.

(21) Appl. No.: 16/932,758

(22) Filed: Jul. 18, 2020

(65) Prior Publication Data

US 2021/0016243 A1 Jan. 21, 2021

Related U.S. Application Data

(60) Provisional application No. 63/026,116, filed on May 17, 2020, provisional application No. 62/969,070, (Continued)

(51) Int. Cl.
*A61L 15/46* (2006.01)
*A61F 13/15* (2006.01)
(Continued)

(52) U.S. Cl.
CPC ............... *B01J 20/20* (2013.01); *A61F 13/15* (2013.01); *A61L 15/08* (2013.01); *A61L 15/14* (2013.01);
(Continued)

(58) Field of Classification Search
CPC .. B01J 20/20; B01J 20/28028; B01J 20/2805; A61F 13/15; A61F 13/2074;
(Continued)

(56) References Cited

U.S. PATENT DOCUMENTS 4,289,513 A 9/1981 Brownhill
4,529,623 A 7/1985 Maggs
(Continued)

FOREIGN PATENT DOCUMENTS

CN 2350026 11/1999
CN 102824365 12/2012
(Continued)

OTHER PUBLICATIONS

US 6,306,487 B1, 04/1994, Karapasha (withdrawn)
(Continued)

*Primary Examiner* — Guy K Townsend
*Assistant Examiner* — Peter Daniel Smith (57) ABSTRACT

The present invention includes the composition and manufacturing of a product to treat various types of infections, and disease ailments. The invention embodies a disposable absorbent or nonabsorbent article comprising an unbound/freely associating adsorbent porous carbonaceous material for the entrapment and/or treatment of pathogens and adverse biological by-products. The product form includes three dimensional carriers such as tampons, panty liners, incontinence pads, diapers, sanitary towels, swabs, cotton balls, pouches, and/or plugs, which contain adsorbent porous carbonaceous material that effectively reduces and/or eliminates adverse situations sourcing from pathogens and harmful biological by-products, including fungi, bacteria, viruses, and parasites. The article is used to treat yeast infections, vaginitis, sexually transmitted diseases, tooth infections, abscess, nail-bed and cuticle infections, and other ailments by way of internal insertion and/or completely covering of the body cavity, mucous membrane, and/or affected areas, creating a clear and direct path for contact with pathogens and adverse biological by-products.

11 Claims, 10 Drawing Sheets

Related U.S. Application Data filed on Feb. 1, 2020, provisional application No. 62/875,511, filed on Jul. 18, 2019.

(51) Int. Cl.

| | | |
|---|---|---|
| *A61L 15/08* | (2006.01) | |
| *A61L 15/14* | (2006.01) | |
| *A61L 15/18* | (2006.01) | |
| *A61L 26/00* | (2006.01) | |
| *B01J 20/20* | (2006.01) | |
| *B01J 20/28* | (2006.01) | |
| *A61F 13/20* | (2006.01) | |
| *A61L 15/20* | (2006.01) | |
| *A61L 15/34* | (2006.01) | |

(52) U.S. Cl.
CPC ............... *A61L 15/18* (2013.01); *A61L 15/46* (2013.01); *A61L 26/0004* (2013.01); *B01J 20/28028* (2013.01); *B01J 20/2805* (2013.01); *A61F 13/2074* (2013.01); *A61L 15/20* (2013.01); *A61L 15/34* (2013.01); *A61L 2209/22* (2013.01); *A61L 2300/108* (2013.01); *A61L 2300/404* (2013.01)

(58) Field of Classification Search
CPC .... A61F 13/104; A61F 13/105; A61F 13/068; A61F 13/066; A61F 13/043; A61F 13/00004; A61F 13/06; A61L 15/08; A61L 15/14; A61L 15/18; A61L 15/46; A61L 26/0004; A61L 15/20; A61L 15/34; A61L 2209/22; A61L 2300/108; A61L 2300/404

See application file for complete search history.

(56) References Cited

U.S. PATENT DOCUMENTS

| | | | |
|---|---|---|---|
| 4,565,727 A * | 1/1986 | Giglia | .................. D21H 13/18 442/325 |
| 6,475,513 B1 * | 11/2002 | Yamada | ............... A61K 8/9789 424/125 |
| 6,899,700 B2 | 5/2005 | Gehling | |
| 7,837,663 B2 | 11/2010 | MacDonald | |
| 8,168,852 B2 | 5/2012 | Quincey | |
| 8,388,996 B2 | 3/2013 | Gehling | |
| 8,748,689 B2 | 6/2014 | Björnberg | |
| 9,555,150 B2 | 1/2017 | Yhien | |
| 9,839,561 B2 * | 12/2017 | Atkinson | .................. A61P 7/04 |
| 10,159,612 B2 | 12/2018 | Stridfeldt | |
| 10,226,752 B2 | 3/2019 | Iida | |
| 2002/0068891 A1 * | 6/2002 | Weathers | ............ A61F 13/0203 604/304 |
| 2002/0128579 A1 * | 9/2002 | Church | ................... A61F 13/00 602/48 |
| 2003/0003095 A1 | 1/2003 | Sunberg | |
| 2003/0093043 A1 * | 5/2003 | Yi | ............................ A61L 15/18 604/374 |
| 2004/0121681 A1 | 6/2004 | Lindsay | |
| 2005/0003725 A1 | 1/2005 | Hill | |
| 2006/0122548 A1 * | 6/2006 | Abrams | ............. A61F 13/0226 602/41 |
| 2013/0053807 A1 | 2/2013 | Taylor | |
| 2013/0164334 A1 | 6/2013 | Quincey, III et al. | |
| 2013/0237933 A1 | 9/2013 | Ko | |

FOREIGN PATENT DOCUMENTS

| | | | |
|---|---|---|---|
| EP | 0053936 | | 6/1982 |
| EP | 0311364 | | 4/1989 |
| JP | 2009096755 A | * | 5/2009 |
| KR | 20090002418 U | | 3/2009 |
| WO | WO2020026209 | | 2/2020 |

OTHER PUBLICATIONS

R.H. McQueen; Book Title: Odour Control of Medical Textiles; Publisher: Of Medical Textiles, Woodhead Pubishing Series and Textiles, 2011, chapter 17 pp. 387-416.

Laurie Swezey; Blog Title: Wound Odor Management: Charcoal Wound Dressing; Publisher: posted by Laurie Swezey Feb. 5, 2016.

Smith-Nephew; Product Title: Carbonet: Odor Absorbent Dressing (Charcoal); Publisher: Smith-Nephew website accessed on Jun. 21, 202.

Dollar Maxi Pad Club; Product Title: Dollar Maxi Pad Club-Bamboo Charcoal; Publisher Maxi Pad Club Website, accessed on Jun. 21, 2020.

Health Products for you; Product Title; Systagenix Actisorb 220 Activated Charcoal Dressing with Silver; Publisher Health Products for You website, accessed on Jun. 21, 2020.

V-Fresh; Product Title: V-Fresh; Publisher V-Fresh website, accessed on Jun. 21, 2020, Medisafe Distribution Inc. Canada.

* cited by examiner

PRODUCTS FOR TREATING INFLAMMATION, INFECTIONS, DISEASE, AND MALODORS CONTAINING ADSORBENT POROUS CARBONACEOUS MATERIAL

FIELD OF THE DISCLOSURE

Examples of the present disclosure generally related to the manufacturing thereof and to products formulated for treating inflammations, infections, diseases, and associated malodor.

BACKGROUND

The disruptive innovation is a cost-effective, over the counter, pharmaceutical-free product that can improve health by reducing various types of inflammations, infections, and diseases by enabling a low-risk self-treatment with better effectiveness and less adverse side effects. Specifically, it includes a disposable absorbent or nonabsorbent article containing unbound/freely associating adsorbent porous carbonaceous material for the entrapment and/or treatment of odor, pathogens, and adverse biological by-products.

In the case of women's health, diseases such as these can have detrimental effects on reproductive health and unborn children. It is well documented that for a variety of reasons, these conditions go largely undetected or untreated. The invention, when incorporated with women's menstrual products, avoids undesirable treatment alternatives such as creams and antibiotics and can act as a preventative for women's health as a normal part of menstruation products.

As related to field-deployed soldiers, minimizing infection in bullet wounds with improved self-treatment options until proper medical attention can be administered is of paramount importance to improve chances of recovery.

Otherwise, Improved and effective self-treatment product options that avoid antibiotics for tooth infections and difficult fungal infections innovate medical therapies and approach.

SUMMARY OF INVENTION

The disruptive innovation is a cost-effective, over the counter, pharmaceutical-free product that can improve health by reducing various types of inflammations, infections, and diseases by enabling a low-risk self-treatment with better effectiveness and less adverse side effects. Specifically, it includes a disposable absorbent or nonabsorbent article containing unbound/freely associating adsorbent porous carbonaceous material for the entrapment and/or treatment of odor, pathogens, and adverse biological by-products.

DETAILED DESCRIPTION

Figure 1:
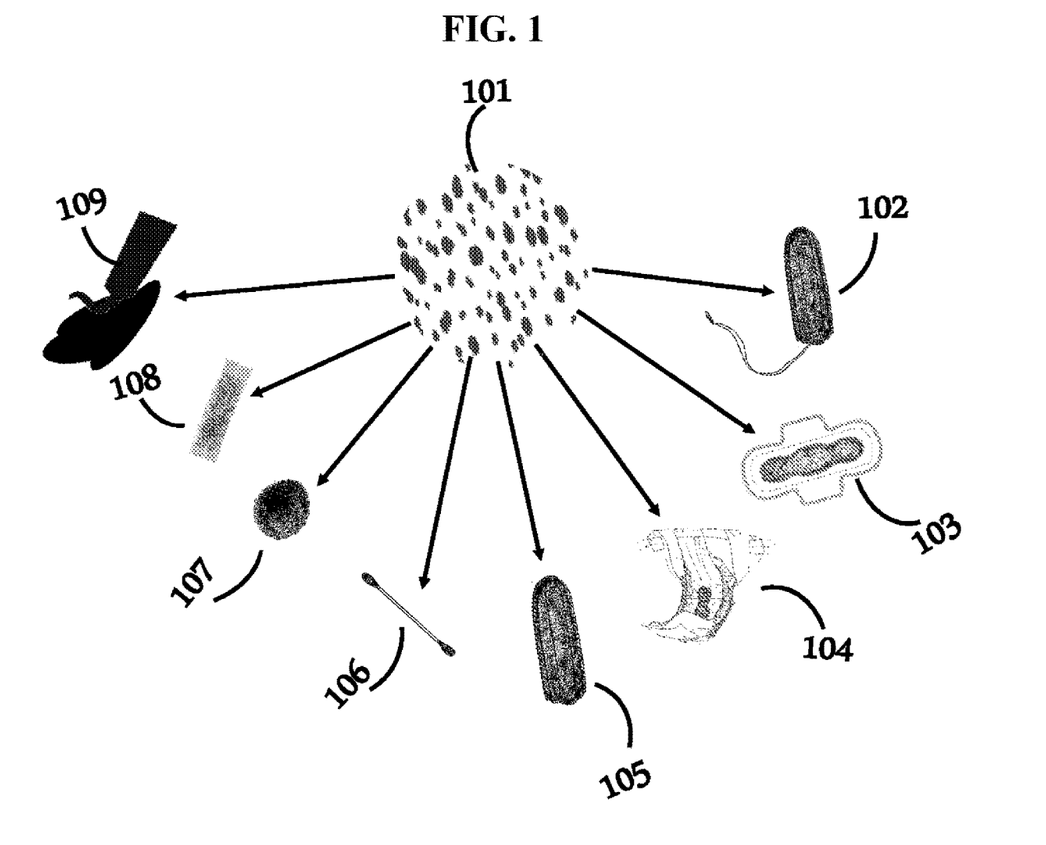
FIG. 1 Shows a flow chart, unbound/freely associating adsorbent porous carbonaceous material (101), a mode for carrying the invention in the form of a tampon (102), a mode for carrying the invention in the form of a feminine hygiene pad, (103), a mode for carrying the invention in the form of a diaper (104), a mode for carrying the invention in the form of a plug (105), a mode for carrying the invention in the form of a cotton swab (106), a mode for carrying the invention in the form of a cotton ball (107), a mode for carrying the invention in the form of a pouch (108), a mode for carrying the invention in the form of a tube of paste, essential oil (109)
Figure 2:
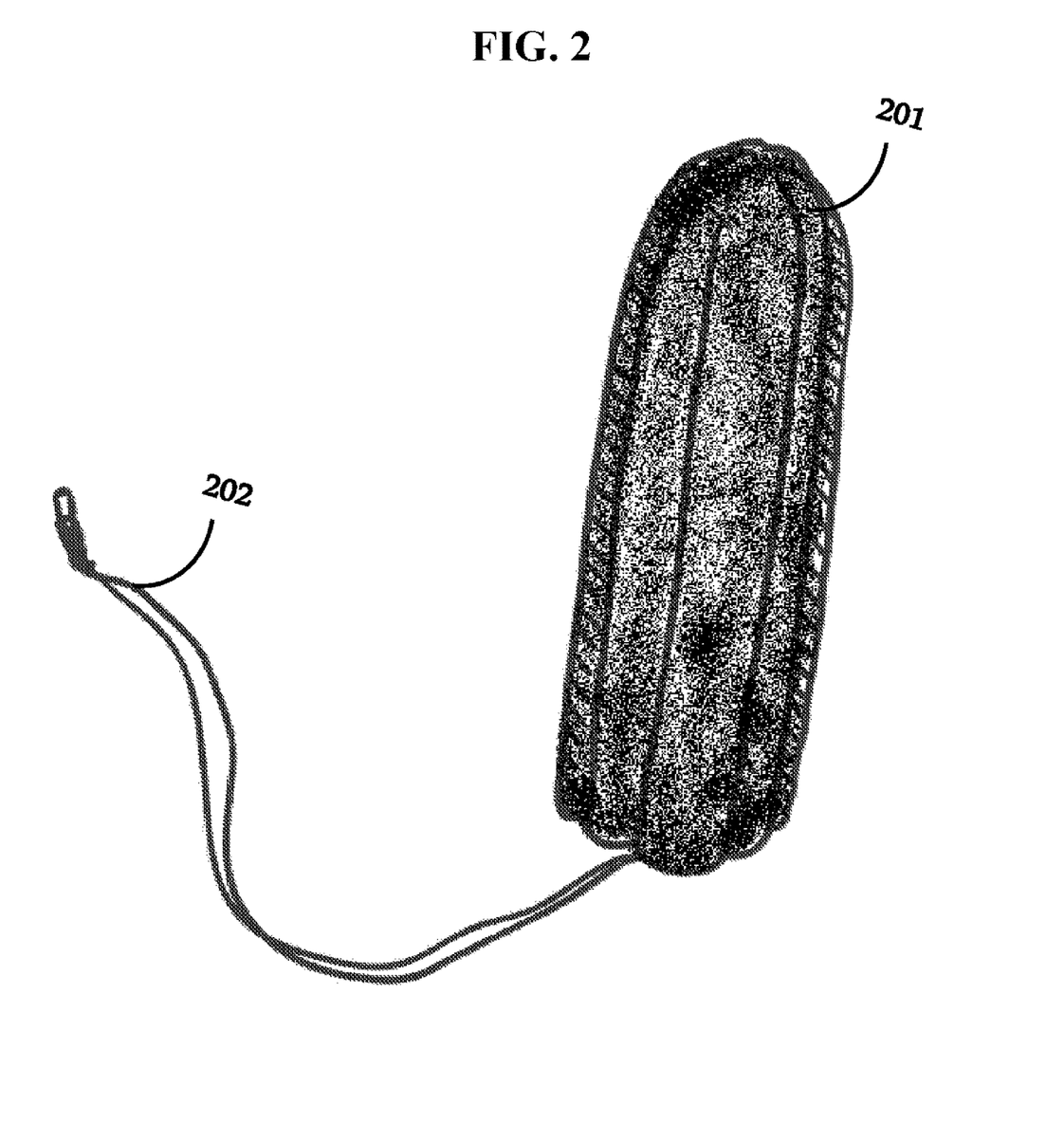
FIG. 2 Shows a mode for carrying the invention in the form of a tampon, the body (201), the string for extraction (202)
Figure 3:
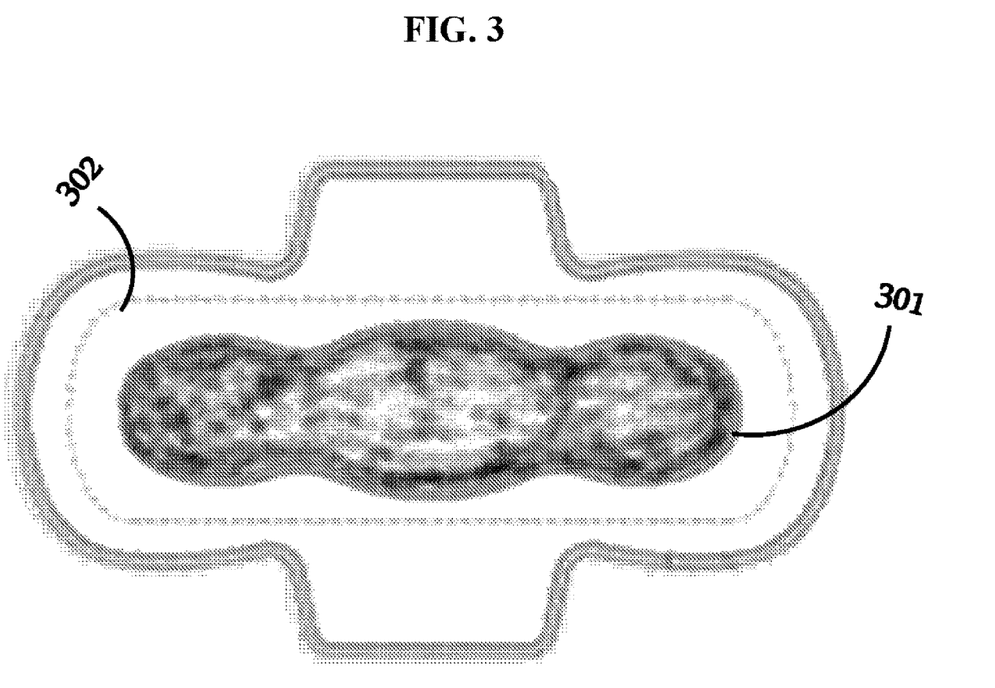
FIG. 3 Shows a mode for carrying the invention in the form of a famine hygiene pad the body of the pad (302) and the inventions placement in the mode (301)
Figure 4:
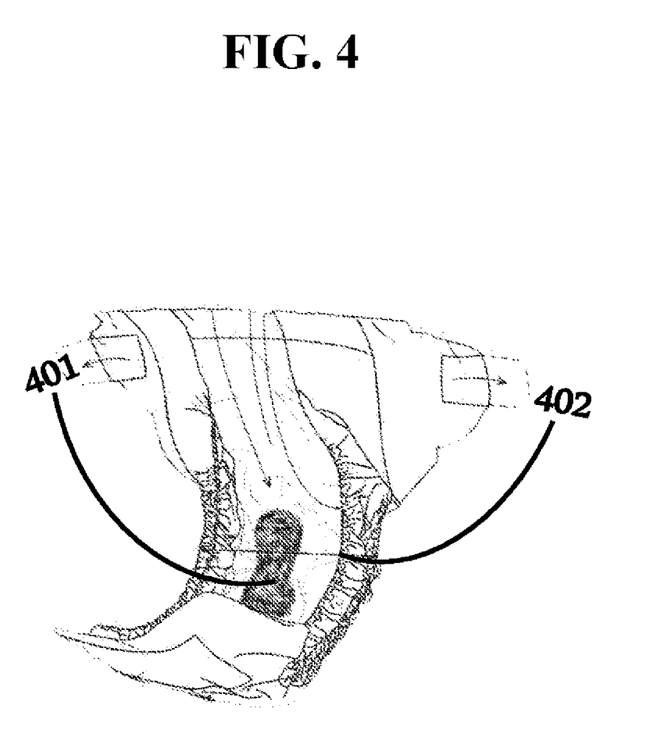
FIG. 4 Shows a mode for carrying the invention in the form of a diaper the body of the diaper (402) and the inventions placement in the mode (401)
Figure 5:
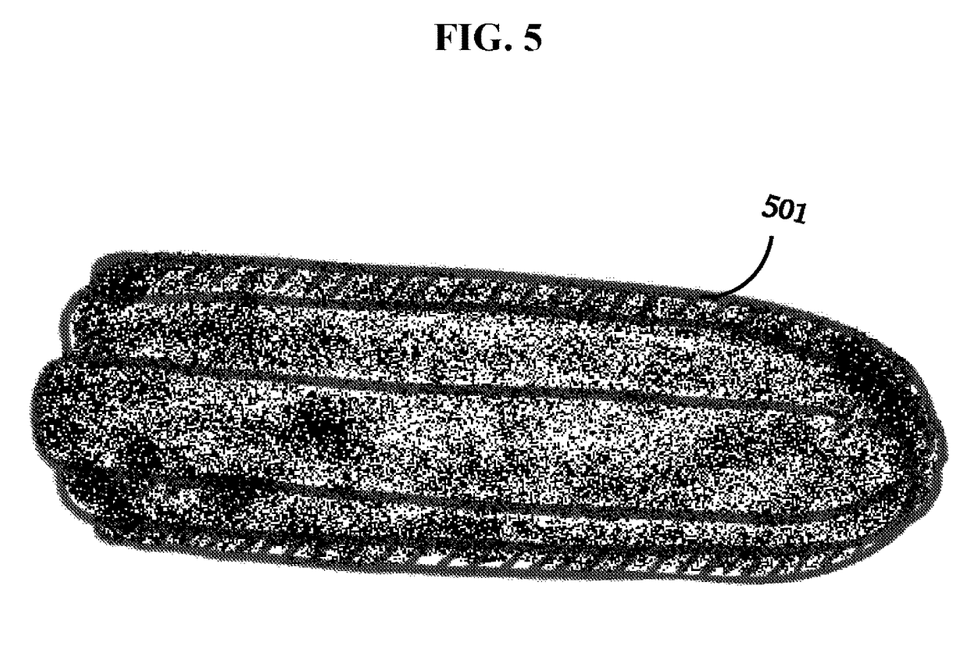
FIG. 5 Shows a mode for carrying the invention in the form of a plug (501), used for nose bleeds etc . . .
Figure 6:
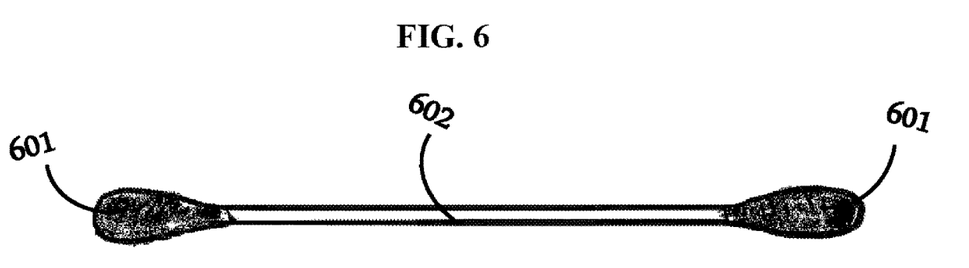
FIG. 6 Shows a mode for carrying the invention in the form of a cotton swab, the body of the swab (602) and the inventions placement in the mode (601)
Figure 7:
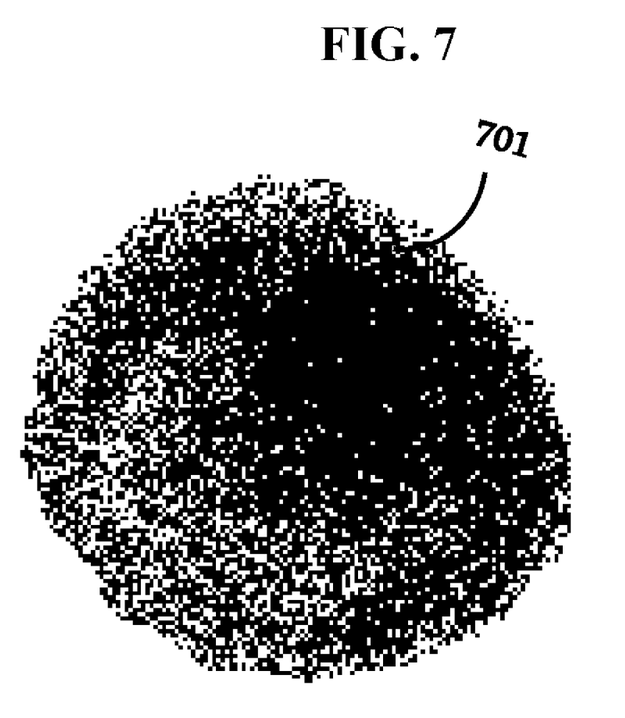
FIG. 7 Shows a mode for carrying the invention in the form of a cotton ball (701)
Figure 8:
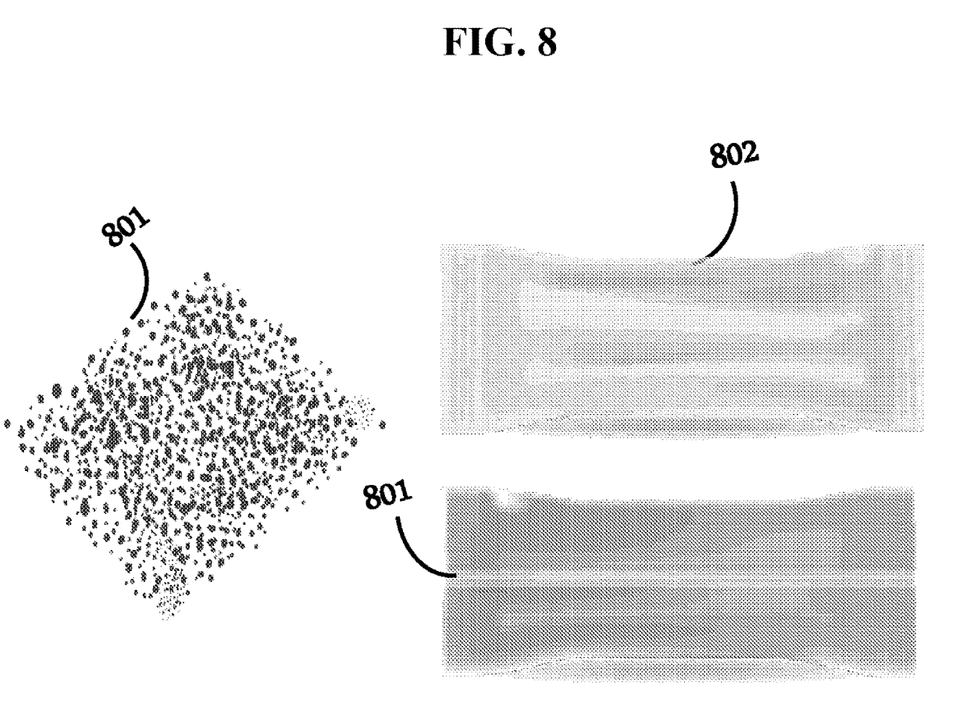
FIG. 8 Shows a mode for carrying the invention in the form of a pouch, the front view (802), the back view (803), and the unbound/freely associating adsorbent unbound/freely associating adsorbent porous carbonaceous material in the center of pouch (801)
Figure 9:
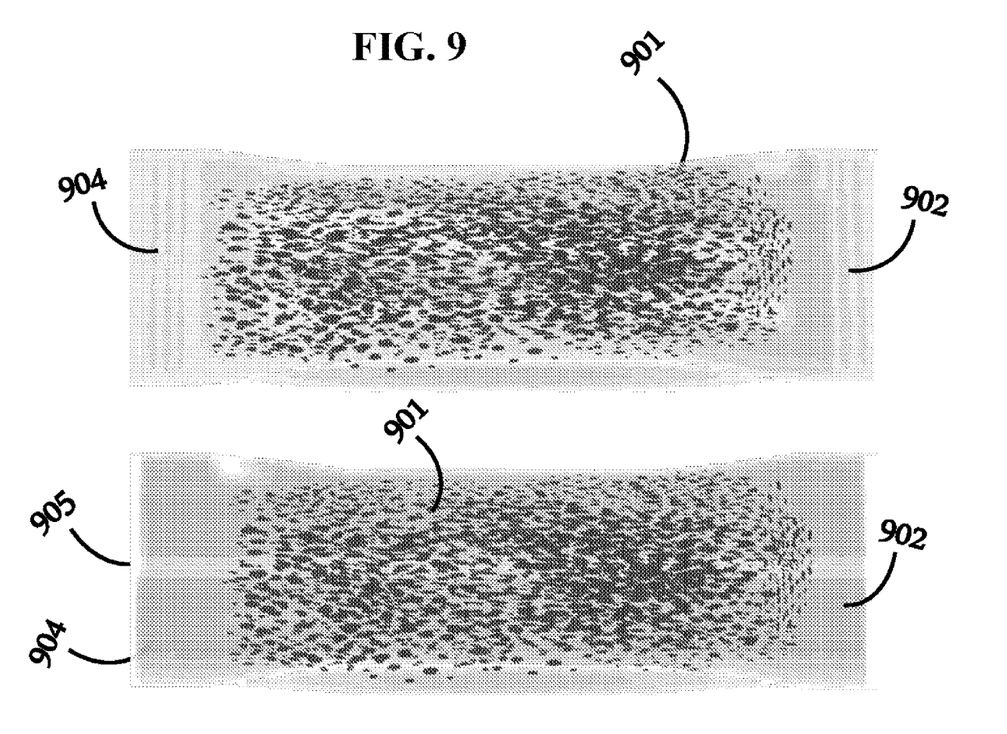
FIG. 9 Shows a mode in FIG. 8 for carrying the invention in the form of a pouch, the front left being a heat seal (904), the front right being a heat seal (902), the invention is placed inside the pouch (901), the back view, left heat seal (904), the middle heat seal (905) and the unbound/freely associating adsorbent porous carbonaceous material in the center (901)
Figure 10:
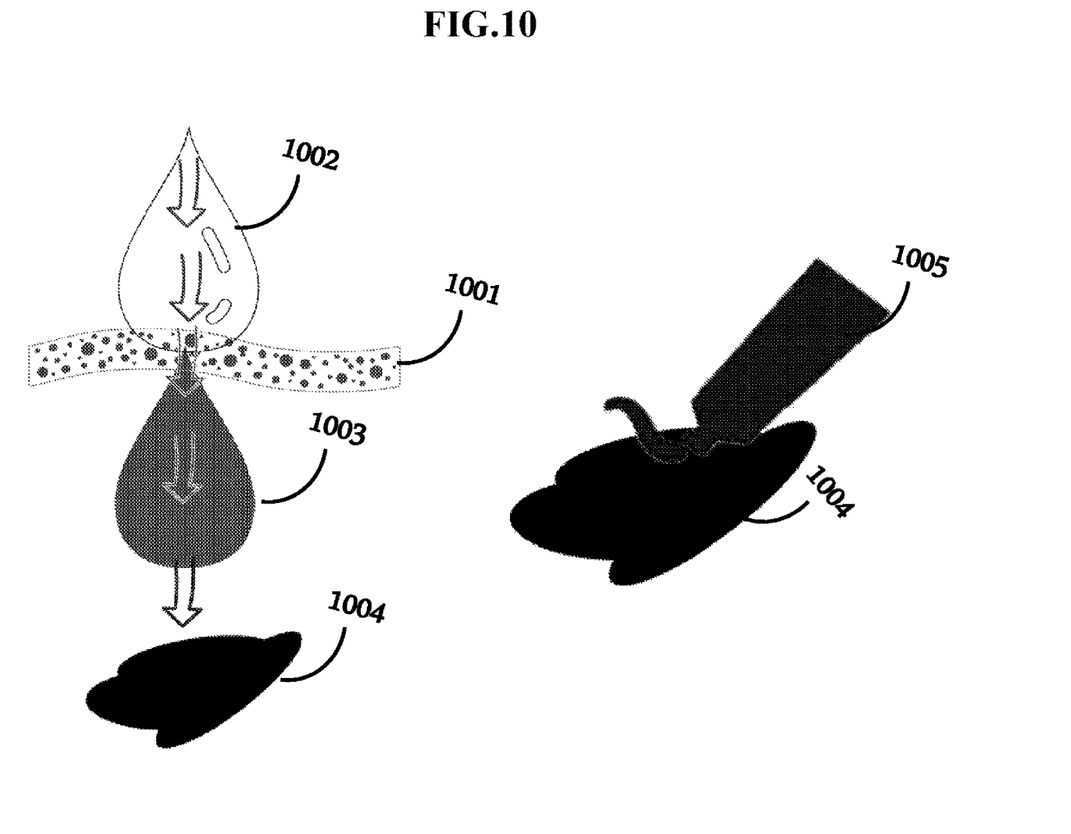
FIG. 10 Shows a mode for carrying the invention in the form of a tube of paste, essential oil (1002), unbound/freely associating adsorbent porous carbonaceous material (1001), mixture of essential oil and unbound/freely associating adsorbent porous carbonaceous material (1003), the paste (1004) Shows a mode for carrying the invention in the form of a tube of paste, (1005).

The invention offers an over the counter (OTC), easily deployable, all-natural prophylactic and/or treatment of odor-causing bacteria and infectious diseases. It is a low-risk self-treatment with better effectiveness, less adverse side effects, without doctor intervention or prescription, it is a cost effective over the counter, pharmaceutical-free product that improves health by reducing various types of infections, and diseases. The invention works by way of contact with body orifices, mucus membranes, and other effected areas, by adsorption meaning the adhesion of fungi, bacteria, viruses, adverse biological by-products, parasites, and sexually transmitted diseases (STDs) to the surface area of the unbound/freely associating adsorbent porous carbonaceous material.

The product may be effectively used for conditions including odor-causing bacteria, bacterial vaginosis, vaginitis, urinary had infections, viral infections, yeast infections, sexually transmitted diseases, nail fungal infections, and dental abscess.

The uniqueness of the product is embodied in the improved effectiveness and the wide array of pathogens and harmful biological side products which it can render inactive. The improved effectiveness is due to the unbound nature of the carbonaceous material, for maximum contact with harmful compounds, and the wide array of pathogens susceptible is due to the selective and adsorptive nature of the carbonaceous material, the lack of negative side effects can be traced back to the minimal and innocuous formulation ingredients, which selectively adsorb or trap harmful compounds over healthful compounds, and do not have 'extra' in that can harm health-supporting compounds or create other adverse chemical reactions and effects.

Loosely coating, saturating, or filling any textile or nonwoven material, inside and/or outside adsorbent porous carbonaceous material creates sufficient presence for effectiveness. The less compressed, the better the effectiveness. This may be achieved via mixing, spraying, injecting, dip-coating, powder-coating, solution-coating, dredging, submersing, tumbling, shaking, compounding, and extrusion techniques at any stage of the production process. The latter of which meaning at initial creation of raw materials, such as fiber or thread spinning, to post-processing of commercial product forms.

While many claim adsorbent effectiveness is due to the specific pore size of activated carbon, which is related to source and processing conditions, we contend that the broad spectrum effectiveness of our product is due to a wide distribution of pore sizes, and that multiple mechanisms enable such broad effectiveness. One additional mechanism includes but is not limited to the physical entrapment of flagellum-like species. Likewise, other allotropes of carbon (similar carbonaceous materials in the same family), whether amorphous or not, have the capability to behave in similar (multiple) ways. These materials include activated charcoal/carbon, carbon black, un-activated charcoal/carbon, graphene, and graphite in powdered and granular forms and mixtures thereof. In the case of activated carbon, activated carbon can be derived from, but not limited to, bamboo, coconut husk, willow peat, hardwood, softwood, coir, lignite, coal, and petroleum pitch. 'Activated' carbon becomes 'activated' by heating at elevated temperature and pressure in the presence of steam, other gases such as argon or nitrogen, or strong acids and bases, or hydroxides, or chlorides. It is generally accepted that processing conditions and carbon source are key variables that impart the resulting pore size. For this work, sources of activated carbon include but are not limited to industrial grade activated carbon from hardwoods and coal, and medical grade ingestible activated carbon from coconut shells.

The invention comprising of an absorbent or a nonabsorbent material in any form, that contains adsorbent porous carbonaceous material for the entrapment, extraction and/or the removal odor-causing bacteria, pathogens, and adverse biological by-products including fungi, bacteria, viruses, parasites, and harmful biological by-products, including sexually transmitted diseases (STD), by way of adsorption via contact with body orifices and/or-mucus membranes and other affected areas.

The product forms including, tampons, panty liners, incontinence pads, diapers, sanitary towels, swabs, cotton balls, pouches, and/or plugs.

The product is used by inserting internally and/or completely covering the body orifice, and/or mucus membrane, nailbeds, cuticles, or otherwise affected areas creating a clear and direct path by which the pathogens, adverse biological by-products, and odor-causing compounds will come in contact with the adsorbent porous carbonaceous material for entrapment and/or treatment. By way of the product contact with body orifices, mucus membranes, and/or other affected areas, the pathogens are rendered ineffective.

The invention has presented no adverse effects due to the adsorptive nature of the porous carbonaceous material and also because it does not inhibit the action of 'good' bacteria, which allow normal healing mechanisms to resume. While the adsorbent porous carbonaceous material renders pathogens inactive and ineffective, it also balances pH.

In certain persistent fungal infections, such as those that infect fingernails and toenails, it has been discovered that combining a paste of carbonaceous material with chosen essential oils, one of which includes but is not limited to, pine oil, and treating the affected area by sealing with a bandage has provided dramatic improvement and restoration of healthy nails.

To date, the invention has been used to adsorb and treat odor-causing bacteria and infections, stemming from fungi, yeast, mold, bacteria, viruses, and/or parasitic pathogens including biological proxies/surrogates of sexually transmitted diseases. In vitro and in vivo experiments have been conducted and support effectiveness. While in vitro experiments are still underway, select volunteer in vivo experiences are recounted below:

Case study 1: Volunteer (person's identity disclosed to the inventor) had a urinary tract infection (UTI) and was experiencing a burning sensation during urination. The subject began to use the treatment tampon on the second day of symptoms, for three successive 4-hour durations, and continued treatment on the third day with two successive 4-hour durations. Immediately after the first application the burning sensation began to diminish. The subject's symptoms completely vanished after the third application and subject has not had any other symptoms since the treatment.

Case Study 2: Volunteer's symptoms began in November 2019 as a sharp pain when urinating with some redness in the area and general discomfort and well as itchiness. The symptoms occurred in phases that would last from 1 day to multiple weeks. Approximately 6 months later the subject began having stomach issues, beginning with lack of appetite, changes in bowel movement frequency, and regular diarrhea. The stomach issues as well as the pain in the vaginal area continued for 2 months and lead to a 20 lb weight loss over that time period. The Volunteer began using the treatment tampon Jun. 30, 2020 and used it daily for 9 days. The pain during urination was completely resolved and stomachache and bowel movements after the first usage. After use on the 2nd day, her appetite began to return and continued to increase. By the $9^{th}$ day of use of the treatment tampon, her appetite completely returned, and the volunteer began to gain weight. Subject left the tampon in around 7 to 10 hours per usage. Only one slight vaginal pain occurred on day 5, but it was resolved by day 6.

Case Study 3: An avid bicyclist and runner complained of vaginal odor-causing bacteria after long periods of cycling and/or running. Prior to the next training activity, she used a treatment tampon. The volunteer reported that all odor-causing bacteria was eliminated by using the treatment tampon during the 2-hour intense exercise period, which had never occurred before.

Case Study 3: A volunteer realized she was getting a yeast infection but could not get to a doctor. After 4 hours of using a treatment tampon, the symptoms were eliminated and did not return.

Case Study 4: After being told that surgery would be required, along with a costly antibiotic, for a severe tooth infection, the inventor created a pouch containing the carbonaceous material, and tucked it in contact with the swollen gum and infected tooth. After 8 hrs. of treatment, within 24 hrs the swelling and infection completely resolved, and surgery was no longer required.

Case Study 5: After multiple rounds of medical treatment for fungal infection on toenails, with no improvement, a volunteer used a paste mixture of carbonaceous material with essential oil and treated overnight the affected areas, sealing with a bandage. After 1 round of overnight treatment, the nailbeds were noticeably improved and over the course of 6 months, healthy toenails replaced the fungal-deformed toenails.

Case Study 6: A volunteer that was particularly susceptible to vaginal bacterial infections used a treatment tampon at the onset of symptoms. It was administered for 8 hours and volunteer reported complete elimination of symptoms.

The invention claims:

1. A method for using a vaginal treatment device for treatment of vaginal related medical conditions, the treatment including adsorption, entrapment, and extraction of disease-causing pathogens from a living being, the method comprising:
providing the vaginal treatment device comprising a menstrual tampon or cup comprising: (a) an unbound, freely associating, adsorbent porous carbonaceous material; (b) a woven and/or nonwoven absorbent textile material;
inserting the vaginal treatment device into the vagina;
preventing external matter from entering the vaginal canal post insertion of the vaginal treatment device by sealing the distal opening of the vagina with a bandage;
treating the vaginal related medical conditions using the inserted vaginal treatment device for an administration duration sufficient for the unbound, freely associating, adsorbent porous carbonaceous material to adsorb, entrap, and extract the disease causing pathogens from the living body; and
removing the inserted vaginal treatment device from the vagina, wherein the unbound, freely associating, adsorbent porous carbonaceous material includes adsorbed, entrapped, and extracted disease causing pathogens from the living body when the inserted vaginal treatment device has been removed.

2. The method of claim 1, wherein the unbound/freely associating adsorbent porous carbonaceous material: (a) comprises at least one of: activated charcoal/carbon; carbon black, an un-activated charcoal/carbon; a graphene; (b) is provided in a granular or a powder form; and wherein the vaginal treatment device further comprises at least one of bamboo; coconut husk; willow peat; lignite; and petroleum pitch.

3. The method of claim 1, wherein the menstrual tampon or cup further comprises: a natural and/or a synthetic material; cotton, wool, polyurethane; nylon; and/or polyester.

4. The method of claim 1, wherein the providing step comprises one or more of injecting; mixing; spraying; dip-coating; powder-coating; solution-coating; dredging; submersing, tumbling; shaking; compounding; infusion; and/or extrusion of the unbound, freely associating, adsorbent porous carbonaceous material to the vaginal treatment device.

5. The method of claim 1, wherein the disease causing pathogens are selected from bacteria; yeast; virus, or a fungus; and wherein the vaginal related medical condition is selected from: a urinary tract infection; a yeast infection; a chlamydia infection; vaginosis; a trichomoniasis infection; a parasite infection; and/or a sexually transmitted disease causing pathogen.

6. The method of claim 1, wherein the administration duration is about: 4-10 hours duration for yeast infections, and/or 8-10 hours for non-yeast infections, of the vaginal related medical conditions.

7. The method of claim 1, wherein the vaginal treatment device is capable of being inserted into a body interface for the adsorption, entrapment, and extraction of the disease-causing pathogens from the living being.

8. The method of claim 1, wherein the vaginal treatment device further comprises at least one essential oil.

9. The method of claim 1, wherein the treating the vaginal related medical condition further comprises eliminating an unpleasant smell or malodor through the adsorption, entrapment, and extraction of the disease causing pathogens from the living body.

10. The method of claim 1, wherein the bandage further comprises a feminine sanitary napkin.

11. The method of claim 10, wherein the feminine sanitary napkin further comprises the or additional unbound, freely associating, adsorbent porous carbonaceous material.

* * * * *